United States Patent [19]

Lecoufle

[11] Patent Number: Plant 7,013

[45] Date of Patent: Sep. 5, 1989

[54] ORCHID LAELIOCATTLEYA VELDORADO POLKA

[75] Inventor: Maurice Lecoufle, St. Leger, France

[73] Assignee: Stewart Orchids, Carpinteria, Calif.

[21] Appl. No.: 212,277

[22] Filed: Jun. 27, 1988

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Howard A. Kenyon

[57] ABSTRACT

A new and distinct variety of orchid, more particularly a Laeliocattleya hybrid plant having flowers of large size and clear coloring with flowers erectly carried on strong sprays. The new variety is distinct from siblings of its grex by its outstanding vigorous plant structure as well as freedom of bloom and the carriage of its flowers. Of primary note with this cultivar is the brilliance of yellow coloring of the flower in contrast to the intensity of the dark maroon color of the labellum.

1 Drawing Sheet

DISCOVERY OF THE NEW VARIETY

The orchid of this application was discovered by the undersigned discoverer as an outstanding member of a large sibling population of the hybrid Laeliocattleya Veldorado (herein abbreviated as Lc. Veldorado). In 1970, Lc. Veldorado was developed in the orchid nursery of Vacherot and Lecoufle at Boissy St. Leger in France. It was made by crossing Lc. Amber Glow × Lc. Colibri. Lc. Amber Glow was the pod parent (mother plant). The resultant grex of this mating was named Lc. Veldorado and was registered by the Vacherot & Lecoufle Nursery with the Orchid Hybrid Registration Committee in London, England in 1976 and published in the 1976–80 volume of Sanders' Orchid Hybrids. The new orchid was registered as by "PFF. V. & L. cross; Lc. Veldorado".

In July, 1976, the new variety appeared as a single outstanding plant among a large population of siblings of Lc. Veldorado, all cultivated and blooming at the nursery in St. Leger, France. The plant of the new variety was immediately recognizable as superior in its flowering and general growth habit to all members of the large population of the hybrid group Lc. Veldorado. After the new variety had been observed for a period of time, its other features of superior growth and flower structure were also noted.

ASEXUAL REPRODUCTION

After its discovery in July, 1976, the original plant was placed in the laboratories of Vacherot & Lecoufle. During the years since 1976, a number of plants of the new cultivar have been asexually produced by the meristem tissue culture process. Portions of tissue called meristems comprised of unspecialized cells, capable of later differentiation, were cut from the plant and developed, under carefully controlled sterile conditions into new individual plants. This has been an ongoing process to cultivate this exceptional variety. The population thus produced is carried under the Code Number OT1Br.

All of the propagations reproduced true to the original in both plant, flower and other characteristics. A substantial cross section have flowered. They are exactly the same as the mother clone, with no signs of mutation. All plants of the new variety have continued to be readily distinguishable from both parentage and all other siblings of Lc. Veldorado in flower quality, plant growth habit and other characteristics. The new variety has been designated as Lc. Veldorado cultivar var. 'Polka'.

DESCRIPTION OF THE PHOTOGRAPHS

The lower photograph is a close-up view of flowers of Lc. Veldorado 'Polka'. The upper photograph shows the plant growth habit to show the vigor, size of the plant and general characteristics.

DESCRIPTION OF THE PLANT

The plant and flowers are illustrated in the color photographs accompanying this application. In some respects, the plant is typical of a yellow Laeliocattleya hybrid. However, because of the difficulty in obtaining yellow Laeliocattleyas of outstanding growth, reliability of bloom and disease resistance, it is unique in these respects. Its strap-like, coriacious leaves are erectly carried and of ovate lanceolate shape. The average leaf is 25 centimeters to 32 centimeters long. They are broader than most yellow Laeliocattleya hybrids. The plant attains a growth on maturity of 35 centimeters to 45 centimeters. However, the plant develops a structure of superior and unusual strength and resilience in all of its parts. The rhizome which joins the pseudobulbs of the plant is moderately short compared to many cattleyas which permits a number of bulbs with leaves in a smaller pot. Additionally, it is the nature of this cultivar to develop more than one new growth from the dormant eyes at the base of the pseudobulbs. The growth is naturally erect without any need to support the leaves and flower stems which is highly advantageous under normal conditions. The strong flower sprays are borne from the axils of the growth and are of superior strength, generally flowering well without supplementary support. Its flowering habit is dependable. The flowers develop from sheaths in the spring and summer growth. Many plants bloom again in the late summer and into the fall. The plants are exceptionally hardy in comparison with similar yellow Laeliocattleya orchids. They have been virus and pathogen free during development, both in the original population of Lc. Veldorado and in the cultivar 'Polka'. The plants in the meristem population of the new variety retain this vigor. The cells apparently have an even chromosome compliment. This is generally indicated by the strong uniform growth habit of the plant and uniform growth of tissue cultured plants of this cultivar. This is generally indicative of an even cytology.

DESCRIPTION OF THE FLOWER

The outstanding merit of the new variety, in addition to the plant vigor and reliability of bloom is the brilliance and clarity of coloring as well as shape of the flowers. The richness of coloration of the sepals and petals is in dramatic contrast to the intense dark maroon purple of the shapely lip. What is especially notable is the excellent carriage of the flowers with each flower in perfect position on the stem—a characteristic not always found in yellow Laeliocattleya and Brassolaeliocattleya hybrids. The margins of the petals have moderate waving which is characteristic in most cattleya hybrids. The sepals have smooth maginal lines and are erectly carried. (The green spot on the tip of the sepals is indicative of a fresh flower. When the green spot disappears this is a sign of aging.)

Sepals and petals are clear medium lemon yellow, best identified from the British Horticultural Colour Chart, as "a lemon yellow" (Lemon B.C.C. 52, Page 4, Vol. II, Swatch 41-4/0). Close horticultural well-known examples are Hypericum Calycinum and fruit of the Eureka lemon. The texture of the sepals and petals is sparkling and clear with no overtones or other markings. The flowers hold their color very well in comparison to others in this line of breeding where the color can often be transient or fugitive. The attractive labellum is in nice balance to the sepals and petals. While it is the focal point of the flower, it is in nice harmony. The lip can best be described as large, shapely with side lobes closed well over the column. Throughout most of its portions it is dark purple, best described as between Peony purple of the B.H.C.C. Page 95, Swatch 729-1 and 729-0 and Doge Purple, Page 96, Swatch 732-1 and 732-0. Horticultural examples are Paeonia Veitchii and Primula hybrid Wanda. In the throat of the labellum and into the interior side lobes is a generous veining of lemon yellow of the same coloration as described above for the sepals and petals. The pollinia in the subject Lc. Veldorado 'Polka' typically of cattleyas is carried on the tip of the column (sex organ) and cannot be seen as it is contained in the anther sac. The stigmatic cavity on cattleyas is on the tip and underside of the column which is in the center of the flower in orchids, particularly cattleyas. The ovary of the subject matter is the stem of the flower itself which is characteristic indicative of all orchids. Botanically, the term is "inferior" to the flower (below the flower). While Lc. Veldorado 'Polka' may be a tetraploid and could be used for further breeding its exact chromosome count has not been determined. Therefore, no claim is made in the patent application for a specific genetic make-up. The propensity of Lc. Veldorado 'Polka' to shed pollen and set seed whether selfed or crossed is not set forth. Orchids do not "shed pollen" as they are pollinated via mechanical means only. In nature, insects in the main. In cultivation the waxy pollen is transferred with tweezers and toothpicks. Very rarely is an orchid cleistogamous (self pollinating).

The flowers of the variety are larger and stronger in structure than the average cultivar in this line of breeding. The flowers average 5 centimeters in petal width with a total span of approximately 12½ centimeters. The new variety can carry as many as 4 flowers on each spray on a mature, well-grown plant. The petals are flat and well carried somewhat forward in contrast to other cultivars of this grex and line of breeding. They are carried without twisting, turning or recurving. The sepals and petals are in symmetrical balance to the lip and create a good round shape to the flower as a whole.

The blooming season is primarily throughout the summer months well into the fall. Its flowering can vary according to cultural conditions where it is grown and sometimes has a midwinter bloom.

The vigor of the cultivar, quality and richness of color of the flowers, freedom of bloom, season and other desirable characteristics of this new cultivar make it of exceptional value for plant sales or commercial cut flower production.

The descriptions for this plant application follow the rules of the International Commission of Nomenclature. The handbook of the American Orchid Society Orchidists glossary is used as a reference. The exceptional vigor of this particular cultivar, excellent blooming season, reliability and freedom of bloom are characteristics which set this particular cultivar above not only the siblings in the grex, but other gregi in this entire line of breeding or other lines of breeding.

What is claimed is:

1. A new and distinct variety in the hybrid genus Laeliocattlya, as described and illustrated, discovered as a superior variety of the grex LC. Veldorado and in particular the cultivar 'Polka', is characterized by a combination of clearness of coloring, superior flower substance, size, shape and further characterized by its exceptional vigor, reliability of bloom, and lasting qualities and to further support the claim of superiority, a plant of this cultivar was exhibited in England before the Orchid Committee of The Royal Horticultural Society where it received an Award of Merit with a two-thirds vote of the Committee who voted this recognition for its superior flower quality.

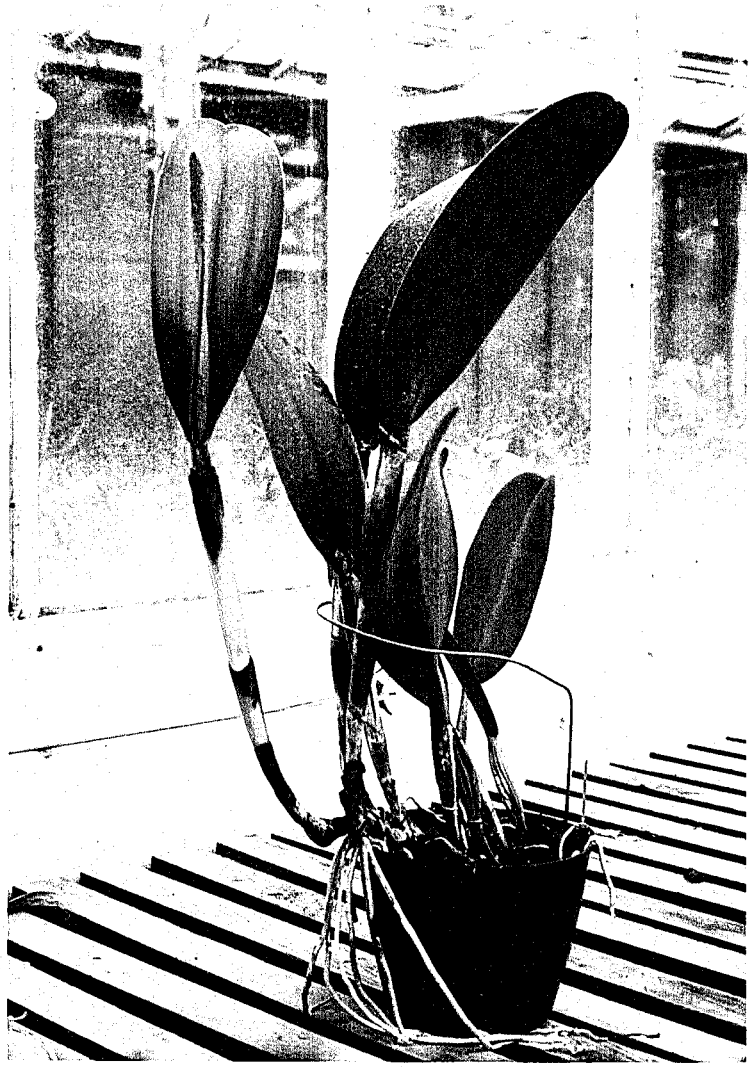
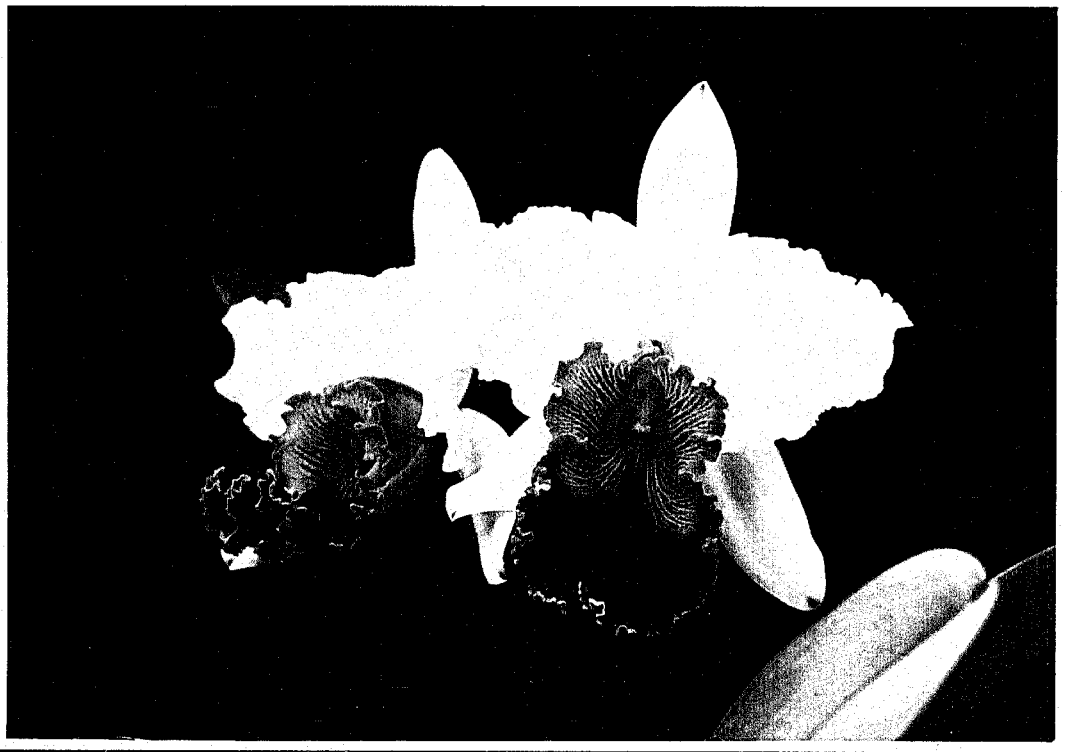

* * * * *